United States Patent [19]

Aparicio et al.

[11] 4,031,243

[45] June 21, 1977

[54] 2-(4-ISOBUTYL PHENYL)BUTYRIC ACID, SALTS THEREOF, AND PHARMACEUTICAL COMPOSITIONS CONTAINING THE SAME

[75] Inventors: Luis Aparicio; Nenesio Gayo; José Ma Carretero; José Luis Martin; Armando Ron, all of Madrid, Spain

[73] Assignee: Juste, S.A. Quimico-Farmaceutica, Madrid, Spain

[22] Filed: July 3, 1975

[21] Appl. No.: 593,059

[52] U.S. Cl. .................. 424/317; 260/247.2 R; 260/515 R; 424/248.53
[51] Int. Cl.$^2$ .................. A61K 27/00; A61K 31/19
[58] Field of Search .................. 424/317, 248.53; 260/515 R, 247.2

[56] References Cited

UNITED STATES PATENTS 3,625,984  12/1971  Levine .......................... 260/515 R

OTHER PUBLICATIONS

Chem. Abst., vol. 77, 96977n (1972).

*Primary Examiner*—Stanley J. Friedman
*Attorney, Agent, or Firm*—Michael J. Striker

[57] ABSTRACT

2-(4-Isobutylphenyl)butyric acid and pharmaceutically acceptable salts thereof, processes for their production, and pharmaceutical compositions containing the same are disclosed. The compounds have antiinflammatory, analgesic and antipyretic properties.

9 Claims, No Drawings

2-(4-ISOBUTYL PHENYL)BUTYRIC ACID, SALTS THEREOF, AND PHARMACEUTICAL COMPOSITIONS CONTAINING THE SAME

SUMMARY OF THE INVENTION

The present invention pertains to 2-(4-isobutylphenyl) butyric acid having the formula

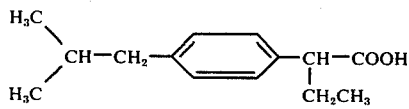

pharmaceutically acceptable salts thereof, and processes for their production. This acid and its salts have antiinflammatory, analgesic and antipyretic properties without disadvantages that are associated with aspirin, phenylbutazone, and adrenocorticosteroids that are presently used as antiinflammatory, analgesic and antipyretic agents in human and animal medication. The compounds have a very low degree of toxicity and have essentially no irritating effects on the gastric lining even when used for long periods of treatment and in this respect are much less ulcerogenic than agents now used for these purposes.

The melting point of 2-4(4-isobutylphenyl)butyric acid is 50°–52° C, whereas that of its sodium salt is 188°–191° C. For this reason, the acid is preferably dispensed in the form of capsules or suppositories whereas the sodium salt and salts with other nontoxic alkali-metal, alkaline-earth metal, and organic bases can be dispensed in the form of tablets, powders or solutions.

2-(4-Isobutylphenyl)butyric acid and its salts can be produced by hydrolysis of 4-isobutylphenylacetonitrile or an alkyl ester of 2-(4-isobutylphenyl)-2-(ethoxycarbonyl)butyronitrile which can be prepared from 4-isobutylphenylacetonitrile. 4-Isobutylphenylacetonitrile, from which esters of 2-(4-isobutylphenyl)cyanoacetic acid can be prepared, can be made by reaction of an alkali-metal cyanide with 4-isobutylbenzyl chloride which latter can be made by passing hydrogen chloride through a suspension of paraformaldehyde and anhydrous zinc chloride in isobutylbenzene, or by a similar chloromethylation reaction of isobutylbenzene.

DETAILED DESCRIPTION AND PREFERRED EMBODIMENTS OF THE INVENTION

The invention is further described in connection with the examples which follow, which were selected solely for the purposes of illustration and are consequently not to be construed as restrictive of the invention or its scope. Methods for the preparation for the 4-isobutylphenylacetonitrile and ethyl 2-4(4-isobutylphenyl)cyanoacetate that are required for the preparation of the compounds disclosed and claimed herein are described in Preparations 1 and 2 that follow.

Preparation 1: 4-Isobutylphenylacetonitrile

4-Isobutylphenylbenzyl chloride was prepared by passing a stream of hydrogen chloride into a suspension of parabormaldehyde and anhydrous zinc chloride in isobutylbenzene. A mixture of 137 grams (0.75 mol) of 4-isobutylbenzyl chloride thus prepared, 44.1 grams (0.90 mol) of sodium cyanide, 216 grams of 99% ethanol, and 81.3 grams of water in a flask provided with a stirrer and reflux condenser was heated to and maintained at reflux temperature while it was continuously stirred for a period of 6 hours, during which the mixture became reddish-black in color. From this mixture, 215 milliliters of ethanol and water was then distilled and the residue was filtered. The solids that were separated by filtration were washed with 100 milliliters of diethyl ether and the ether washings were combined with the original filtrate, to which 800 milliliters of water was then added. The organic phase was then separated from the aqueous phase, washed with five 400-milliliter portions of water and dried over anhydrous sodium sulfate. The ether was evaporated from the dried organic phase by vacuum distillation and the residue which distilled between 130° and 132° C at a pressure of 7 millimeters of mercury was collected.

In this manner, between 100 and 113 grams of 4-isobutylacetonitrile which may also be referred to as 4-isobutylbenzene cyanide, which is equivalent to a yield between 77 and 80% of the theoretical, was obtained.

Preparation 2: Ethyl 2-(4-isobutylphenyl)cyanoacetate

A mixture of 52 grams (0.31 mol) of 4-isobutylphenylacetonitrile (Preparation 1) and 230 grams (1.95 mols) of diethyl carbonate was heated in a flask provided with a thermometer, stirrer, dropping funnel, and distillation column having a length of 19 centimeters filled with Fenske rings. When the temperature of the mixture had reached 90° C, a solution of sodium ethoxide in ethanol that was freshly prepared from 9.2 grams (0.4 mol) of sodium metal and 200 milliliters of ethanol was added drop by drop from the dropping funnel while the vapors formed were permitted to distill through the distillation column. After the temperature reached between 120° and 130° C, no further vapors were distilled and the mixture was stirred vigorously for an additional period of 1 hour. Thereafter, the mixture remaining in the flask was cooled and the flask was surrounded with cracked ice and a solution of 35 milliliters of glacial acetic acid in 130 milliliters of water was added thereto with stirring. The organic phase was then separated from the aqueous phase. The aqueous phase was extracted with ether and the extract was combined with the organic phase, which was then successively washed with a saturated aqueous solution of sodium bicarbonate and water and dried over anhydrous magnesium sulfate. The dried liquid was then filtered to separate the solids therefrom and the filtrate was distilled under vacuum, the fraction distilling between 150° and 155° C at a pressure of 1 millimeter of mercury, which is the ethyl 2-(4-isobutylphenyl)cyanoacetate, was collected.

There was thus obtained 58 grams of colorless product which is equivalent to a yield of 80% of the theoretical.

EXAMPLE 1

2-(4-Isobutylphenyl)butyric acid and its sodium salt

To a solution of 6.7 grams (approximately 0.17 mol) of sodium amide ($NaNH_2$) in 100 milliliters of anhydrous diethyl ether contained in a 250-milliliter glass distilling flask that was provided with a stirrer, reflux condenser, dropping funnel, and drying tube filled with anhydrous calcium chloride, was gradually added during the course of approximately 1 hour by means of the dropping funnel, 26 grams (approximately 0.15 mol) of 4-isobutylphenylacetonitrile (Preparation 1 hereinbefore) while the mixture was stirred and heated under gentle reflux.

After all of the 4-isobutylphenylacetonitrile had been added, the mixture was heated under gentle reflux for a further period of 15 minutes, after which 23.4 grams (approximately 0.15 mol) of ethyl iodide was slowly added dropwise thereto from the dropping funnel. After completion of the addition of the ethyl iodide, the mixture was heated under gentle reflux for an initial period of 15 minutes, after which it was diluted with an equal volume of water and shaken. The two layers that formed were separated and the aqueous layer was then extracted with two 50-milliliter portions of diethyl ether. The ether extracts were combined and then washed with two 80-milliliter portions of water and dried over anhydrous magnesium sulfate.

The dried ether extract was then distilled at a subatmospheric pressure. In this manner, 25 grams of a clear transparent uncolored liquid having a boiling point of 118°–122° C at a pressure of 1 millimeter of mercury, which consisted of 2-(4-isobutylphenyl)butyronitrile, was collected. This yield was equivalent to 83% of the theoretical.

A mixture of 40 grams (0.2 mol) of 2-(4-isobutylphenyl)butyronitrile as thus prepared and 78 milliliters of a freshly prepared solution of sodium hydroxide that was prepared by dissolving 28 grams of sodium hydroxide in 25 milliliters of distilled water and the volume of which was brought to 100 milliliters by addition thereto of methanol, was heated under gentle reflux in a flask provided with a stirrer and reflux condenser while the mixture was stirred during a period of 9 hours. From the mixture the methanol and a portion of the water were distilled and the mixture was then cooled, whereupon crystals began to separate. The mixture was then diluted with 150 milliliters of water and extracted with two 25-milliliter portions of diethyl ether. The remaining aqueous solution containing the sodium salt of 2-(4-isobutylphenyl)butyric acid was then saturated with sodium chloride until the salt started to precipitate. The solution was then cooled to 5° C and the precipitated salt was separated by filtration, recrystallized from isopropanol, and dried in a vacuum desiccator at a pressure of 1 millimeter of mercury until it had attained a constant weight.

In this manner, 32 grams of sodium 2-(4-isobutylphenyl)butyrate having a melting point of 188°–191° C, which is equivalent to a yield of 67% of the theoretical, was obtained.

Dilute hydrochloric acid (19% by weight of hydrogen chloride) was slowly added to a cold solution of 25 grams of the sodium 2-(4-isobutylphenyl)butyrate thus prepared in 100 milliliters of water until the hydrogen-ion concentration of the solution corresponded to a pH of 1.0. The oil which precipitated was then allowed to solidify to a white solid by standing in a refrigerator. The white solid was then separated by filtration, dried, and recrystallized from petroleum ether. It had a melting point of 50°–52° C, and its elementary analysis corresponded closely to the empirical formula $C_{14}H_{20}O_2$. The amount thus obtained was equivalent to a yield of 95% of the theoretical based upon the starting sodium salt.

EXAMPLE 2

2-(4-Isobutylphenyl)butyric acid and its sodium salt

Five (5.0) grams of small pellets of sodium metal were added slowly with stirring to 150 milliliters of absolute ethanol contained in a 700-milliliter distilling flask provided with a gas-inlet tube, stirrer, dropping funnel, reflux condenser and thermometer, while a current of nitrogen gas was passed therethrough so as to blanket the solution from the atmosphere. After all of the sodium metal had been dissolved and while the solution was maintained at a temperature of 50° C, a solution of 52 grams (approximately 0.21 mol) of ethyl 2-(-4-isobutylphenyl)cyanoacetate (Preparation 2 hereinbefore) in 50 milliliters of absolute ethanol was added dropwise thereto from the dropping funnel while the mixture was stirred.

Subsequently, 81 grams (approximately 0.52 mol) of ethyl iodide was gradually added to the mixture with stirring, after which the introduction of nitrogen gas into the mixture was discontinued and the mixture was heated for a period of 2.5 hours under gentle reflux. Thereafter, the ethanol and excess ethyl iodide were expelled from the mixture by distillation followed by vacuum distillation and the residue was then diluted with three times its volume of water and shaken therewith. The 2-(4-isobutylphenyl)-2-(ethoxycarbonyl)butyronitrile was then extracted from the mixture with three 50-milliliter portions of diethyl ether, the extracts were combined, washed with a 20% aqueous solution of sodium bisulfate and dried over anhydrous magnesium sulfate. The ether was then expelled from the extract by distillation and the residue was distilled at a subatmospheric pressure, yielding 45 grams of a fraction containing 2-(4-isobutylphenyl)-2-(ethoxycarbonyl)butyronitrile having a boiling point of 150°–155° C at a pressure of 3 millimeters of mercury, which is equivalent to approximately 0.165 mol or 78% of the theoretical yield based on the original ethyl 2-(4-isobutylphenyl)cyanoacetate.

In a 2-liter flask provided with a stirrer and reflux condenser a solution of 129 grams (approximately 0.47 mol) of 2-(4-isobutylphenyl)-2-(ethyoxycarbonyl)butyronitrile in 980 milliliters of a 20%-by-weight solution of potassium hydroxide in methanol was heated with stirring at a temperature of 40° C. for a period of 1 hour. The mixture was then heated under gentle reflux with stirring for an additional period of 3 hours, during which a white solid precipitated. This mixture was then poured into 1.5 liters of water and acidified with an aqueous solution of hydrochloric acid (concentrated hydrochloric acid diluted with an equal volume of water) to a hydrogen-ion concentration corresponding to a pH of 2.5, while carbon dioxide was evolved therefrom. The aqueous mixture was then extracted with diethyl ether, the extracts were washed successively with a saturated solution of sodium bicarbonate and water, dried over anhydrous magnesium sulfate, and distilled at a subatmospheric pressure, to yield 86.5 grams of a fraction consisting of 2-(4-isobutylphenyl)butyronitrile having a boiling point of 124°–128° C at a pressure of 1.5 millimeters of mercury, which is equivalent to approximately 0.43 mol and a yield of 91% of the theoretical based on the original 2-(4-isobutylphenyl)-2-(ethoxycarbonyl)butyronitrile.

The 2-(4-isobutylphenyl)butyronitrile was converted to sodium 2-(4-isobutylphenyl)butyrate and subsequently to 2-(4-isobutylphenyl)butyric acid in the same manner as described in Example 1 hereinbefore.

EXAMPLE 3

Morpholine 2-(4-isobutylphenyl)-butyrate

Five (5.0) grams of 2-(4-isobutylphenyl)butyric acid (0.0027 mol) in 20 milliliters of anhydrous diethyl ether was added to a solution of 3.2 grams (0.0264 mol) of morpholine in 20 milliliters of anhydrous diethyl ether and the mixed solution was stirred for 5 minutes and placed in a refrigerator overnight, during which period a white solid precipitated. This solid was separated by filtration and dried. It had a melting point of 69°–71° C and a nitrogen content of 4.60% by weight which is in close agreement with a calculated nitrogen content of 4.56% for morpholine 2-(4-isobutylphenyl)-butyrate having the empirical formula $C_{18}H_{29}O_3N$.

Other alkyl esters of 2-(4-isobutylphenyl)cyanoacetic acid can be used in place of ethyl 2-(4-isobutylphenyl)cyanoacetate. The proportions of reactants and the reaction conditions can also be varied within wide ranges in known manner as specified in the foregoing examples.

Other organic bases that may be used for the preparation of pharmaceutically acceptable salt from the acid as described in Example 3 hereinbefore include piperidine and 2-dimethylaminoethanol.

UTILITY AND RESULTS OF TESTS OF THE COMPOUNDS 2-(4-Isobutylphenyl)butyric acid and its salts have antiinflammatory, analgesic and antipyretic properties. They have a very low degree of toxicity and have no irritating effect on the gastric lining.

These compounds are intended for use in human and animal medication and are adapted primarily for oral administration in the form of capsules, tablets, or syrups, or rectally in the form of suppositories. A suitable unit-dosage form of sodium 2-(4-isobutylphenyl)butyrate is a capsule containing between 100 and 300 milligrams thereof in admixture with talcum and magnesium stearate, in which form the compound dissolves well in the stomach without producing a gastric upset or irritation. A specific example of such a composition that is adapted for administration four times daily is a gelatin capsule containing the following ingredients:

| | |
|---|---|
| Sodium 2-(4-isobutylphenyl)butyrate | 200 milligrams |
| Talc | 35 milligrams |
| Magnesium stearate | 5 milligrams |

Other suitable pharmaceutical compositions are exemplified by the following:

Syrup for oral administration, each 5 milliliters of which contains 200 milligrams of the compound:

| | | |
|---|---|---|
| Sodium 2-(2-isobutylphenyl)butyrate | 4.0 | grams |
| Sugar | 85.0 | grams |
| Flavoring substances | 0.05 | gram |
| Water, quantum sufficit | 100 | milliliters |

A suitable formulation for the preparation of suppositories is the following:

| | |
|---|---|
| Sodium 2-(4-isobutylphenyl)butyrate | 400 milligrams |
| Mono,di, and triglycerides of vegetable fatty acids | 2 grams |

The results of animal tests are tabulated hereinafter. The tests that were used are standard tests which are described in the cited publications.

TABLE 1–3

Antiinflammatory activity: Acute rat paw edema test

Described by C. H. Winter, E. A. Risley and G. W. Nuss in a paper entitled "Carageenin-induced edema in hind paw of the rat as an assay for antiinflammatory drugs", published in Proc. Soc. Exp. Biol. Med., volume 111, page 544 (1962).

$ED_{50}$ in this test represents the effective dose in milligrams per kilogram of body weight that is required to inhibit edema produced by administration of carageenin to the rat.

A compound having a smaller $ED_{50}$ is more effective than one having a higher $ED_{50}$ in this and all other tests that are referred to herein.

TABLE 4

Antiinflammatory activity: Formation of granulation tissue in the rat

Described by N. Pisanti, G. Volterra and A. Meli, in a paper entitled "Pharmacological data on a new antiinflammatory agent", published in Il Farmaco(Ed. Scientifica) vol. 38, page 51 (1973).

$ED_{50}$ in this test represents the effective dose in milligrams per kilogram of body weight that is required to inhibit by an increment of 50% the formulation of granulation tissue in the rat.

TABLE 5

Analgesic activity: Hot-plate test

Described by N. B. Eddy and A. Leimbach in J. Pharmacology, volume 107, page 385 (1953).

$ED_{50}$ in this test represents the effective dose in milligrams per kilogram of body weight that is required to increase by 50% the reaction time of the animal.

TABLE 6

Analgesic activity: Tail pinch test in the mouse

Described by F. Haffner in Deutsch. med. Wochsch., volume 55, page 731 (1969).

$ED_{50}$ in this test represents the effective dose in milligrams per kilogram of body weight that is required to increase the reaction time by a factor of at least 3 over the reaction time of the same animal before the test substance had been administered.

TABLE 7

Ulcerogeneric assay

Described by S. Wong, J. F. Gardocki and T. P. Pruss in J. Pharm. Exper. Therap., Volume 181, page 127 (1973).

$UD_{50}$ represents the dose in milligrams per kilogram of body weight that is based upon a point scale as follows:

0 — no ulcers
1 — redness of mucosa
2 — pin-point ulcers
3 — ulceration with craters

TABLE 1

ANTIINFLAMATORY ACTIVITY ACUTE RAT PAW EDEMA TEST

| Treatment | Number of Animals | Dose mg/kg | Administration | Increment of Edema ± SEM | % Inhibition | Lineal Regression | $ED_{50}$ mg/kg |
|---|---|---|---|---|---|---|---|
| Control | 20 | — | — | 14.80 ± 0.94 | — | — | — |
| 2-(4-Isobutyl-phenyl)butyric acid | 60 | 120 | Oral | 7.25 ± 1.00 | 51.01 | b = 30.96 | |
|  | 60 | 180 | Oral | 6.20 ± 0.84 | 58.10 | a = −13.96 | 116.38 |
|  | 60 | 240 | Oral | 5.00 ± 0.97 | 66.21 | y = 30.96 × −13.96 | |
| Phenylbutazone | 60 | 120 | Oral | 6.50 ± 1.02 | 56.08 | b = 30.93 | |
|  | 60 | 180 | Oral | 5.20 ± 0.41 | 64.86 | a = −8.37 | 77.11 |
|  | 60 | 240 | Oral | 4.30 ± 0.89 | 70.94 | y = 30.93 × −8.37 | |

TABLE 2

ANTIINFLAMATORY ACTIVITY ACUTE RAT PAW EDEMA TEST

| Treatment | Number of animals | Dose mg/kg | Administration days | Administration | Increment of edema ± SEM | % Inhibition | Lineal regression | $ED_{50}$ |
|---|---|---|---|---|---|---|---|---|
| Control | 20 | — | — | — | 15.35 ± 0.31 | — | — | — |
| 2-(4-Isobutyl-phenyl)butyric acid | 40 | 120 | 6 | Oral | 11.66 ± 0.67 | 24.03 | b = 118.14 | |
|  | 40 | 180 | 6 | Oral | 9.06 ± 0.39 | 40.97 | a = −222.75 | 203.56 |
|  | 40 | 240 | 6 | Oral | 6.13 ± 0.35 | 60.06 | y = 118.14 × −222.75 | |
| Phenylbutazone | 40 | 120 | 6 | Oral | 10.00 ± 0.73 | 34.85 | b = 110.75 | |
|  | 40 | 180 | 6 | Oral | 8.86 ± 0.36 | 42.28 | a = −198.96 | 176.98 |
|  | 40 | 240 | 6 | Oral | 4.66 ± 0.54 | 69.64 | y = 110.75 × −198.96 | |

TABLE 3

ANTIINFLAMATORY ACTIVITY ACUTE RAT PAW EDEMA TEST

| Treatment | Number of Animals | Dose mg/kg | Administration | Increment of Edema ± SEM | % Inhibition | Lineal Regression | $ED_{50}$ |
|---|---|---|---|---|---|---|---|
| Control | 6 | — | — | 12.50 ± 1.66 | — | — | — |
| 2-(4-Isobutyl-phenyl)butyric acid | 30 | 120 | I.P. | 6.33 ± 0.88 | 49.36 | b = 86.77 | |
|  | 30 | 240 | I.P. | 4.50 ± 1.05 | 64.00 | a = −134.16 | 132.55 |
|  | 30 | 360 | I.P. | 0.88 ± 0.26 | 92.96 | 6 = 86.77 × −134.16 | |
| Phenylbutazone | 30 | 120 | I.P. | 6.83 ± 0.94 | 45.36 | | |
|  | 30 | 240 | I.P. | + four animals | — | — | |
|  | 30 | 360 | I.P. | + five animals | | | |

TABLE 4

ANTIINFLAMATORY ACTIVITY FORMATION OF GRANULATION TISSUE IN THE RAT

| Treatment | Number of animals | Dose mg/kg | Administration | Weight of granulated tissue ± SEM | % Inhibition | Lineal Regression | $ED_{50}$ mg/kg |
|---|---|---|---|---|---|---|---|
| Control | 20 | — | — | 198 ± 3.63 | — | | |
| 2-(4-Isobutyl-phenyl)butyric acid | 40 | 120 | Oral | 176 ± 13.09 | 11.11 | b = 118.38 | |
|  | 40 | 180 | Oral | 130 ± 8.54 | 34.34 | a = −234.32 | 252.20 |
|  | 40 | 240 | Oral | 106 ± 9.97 | 46.46 | y = 98.25 × −187.93 | |
| Phenylbutazone | 40 | 120 | Oral | 167 ± 8.25 | 15.65 | b = 98.25 | |
|  | 40 | 180 | Oral | 128 ± 8.19 | 35.35 | a = −187.93 | 264.04 |
|  | 40 | 240 | Oral | 109 ± 8.77 | 44.94 | y = 98.25 × −187.93 | |

TABLE 5

ANALGESIC ACTIVITY HOT PLATE TEST

| Treatment | Number of Animals | Dose mg/kg | Administration | Reaction time (Seconds) Half ± SEM | % Increase of Reaction time | Lineal Regression | $ED_{50}$ |
|---|---|---|---|---|---|---|---|
| Control | 20 | — | — | 103.3 ± 7.9 | — | — | — |
| 2-(4-Isobutyl-phenyl)butyric acid | 60 | 60 | Oral | 110.6 ± 7.0 | 7.0 | b = 103.08 | |
|  | 60 | 120 | Oral | 139.5 ± 10.7 | 35.0 | a = −179.51 | 162.5 |
|  | 60 | 180 | Oral | 142.3 ± 7.6 | 37.0 | y = 103.08 × −179.51 | |
|  | 60 | 240 | Oral | 184.3 ± 13.1 | 78.4 | | |
| Aspirin | 60 | 120 | Oral | 126.8 ± 13.7 | 22.7 | b = 158.19 | |
|  | 60 | 180 | Oral | 162.6 ± 8.0 | 57.4 | a = −304.21 | 173.4 |
|  | 60 | 240 | Oral | 175.1 ± 5.9 | 69.5 | y = 158.19 × −304.21 | |

TABLE 6

ANALGESIC ACTIVITY
TAIL PINCH TEST IN THE MOUSE

| Composition | Dose (Oral) mg/kg | Number of Animals | Animals Protected | Animals Not protected | % Protection | Lineal Regression | $ED_{50}$ |
|---|---|---|---|---|---|---|---|
| 2-(4-Isobutyl-phenyl)butyric acid | 60 | 20 | 3 | 17 | 15 | b = 122.24 | |
| | 120 | 20 | 10 | 10 | 50 | a = −203.30 | 118.07 |
| | 180 | 20 | 14 | 6 | 70 | y = 122.24 × −203.30 | |
| | 240 | 20 | 18 | 2 | 90 | | |
| Aspirin | 60 | 15 | 2 | 13 | 13.3 | b = 130.68 | |
| | 120 | 15 | 8 | 7 | 53.3 | a = −219.16 | 114.73 |
| | 180 | 15 | 11 | 4 | 73.3 | y = 130.68 × −219.16 | |
| | 240 | 15 | 14 | 1 | 93.3 | | |
| TOTALS | | | | | | | |
| 2-(4-Isobutylphenyl)-butyric acid | | 80 | 45 | 35 | | $X^2$ = 0.058  P: 0.5 N.S. | |
| Aspirin | | 60 | 35 | 25 | | | |

TABLE 7

ULCEROGENIC ASSAY

| Composition | Dose mg/kg/day | No. of experiments | No. of rats | Point score | Correlation coefficient lineal regression | $UD_{50}$ mg/kg |
|---|---|---|---|---|---|---|
| 2-(4-Isobutyl-phenyl)butyric acid | 60 | 2 | 20 | 2 | r = 0.99 | 1.583 |
| | 120 | 2 | 20 | 7 | y = 19.93 × −33.77 | |
| | 240 | 2 | 20 | 14 | | |
| Phenylbutazone | 60 | 2 | 20 | 8 | r = 0.98 | |
| | 120 | 2 | 20 | 17 | y = 39.86 × −63.88 | 226 |
| | 240 | 2 | 20 | 32 | | |

U.S. $_{50}$ Half ulcerogenic dose — dose which produces 50% of the maximum possible score points in one group of rats.

Without further analysis, the foregoing will so fully reveal the gist of the present invention that others can, be applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. 2-(4-Isobutylphenyl)butyric acid or a pharmaceutically acceptable salt thereof.
2. A salt as defined in claim 1 which is an alkali-metal 2(4-isobutylphenyl)butyrate.
3. A salt as defined in claim 1 which is sodium 2-(4-isobutylphenyl)butyrate.
4. A salt as defined in claim 1 which is morpholine 2-(4-isobutylphenyl)butyrate.
5. A pharmaceutical composition having antiinflammatory, analgesic and antipyretic properties comprising 2-(4-isobutylphenyl)butyric acid or a pharmaceutically acceptable salt thereof as defined in claim 1 together with a carrier therefor, the acid or salt being present in an amount from 200 to 400 mg per unit dose.
6. The pharmaceutical composition of claim 5 which is in tablet or capsule form and wherein the carrier is talcum and magnesium stearate.
7. The pharmaceutical composition of claim 5 which is in the form of a syrup and wherein the carrier is in the form of an aqueous sugar solution.
8. The pharmaceutical composition of claim 5 which is in the form of a suppository and includes mono-, di-, and triglycerides of vegetable fatty acids as carrier.
9. A pharmaceutical composition as defined in claim 5 consisting of a gelatin capsule containing approximately 200 milligrams of sodium 2-(4-isobutylphenyl)-butyrate, 35 milligrams of talcum, and 5 milligrams of magnesium stearate.

* * * * *